United States Patent [19]

Flom et al.

[11] 4,368,187

[45] Jan. 11, 1983

[54] SENSITIVE-SKIN CARE REGIME

[75] Inventors: Merlyn G. Flom, Noblesville; Anne M. Herrold, Brownsburg; Joe O. Martin, Martinsville; Anton A. Mentlik, Noblesville; Patricia P. Warrick, Indianapolis, all of Ind.

[73] Assignee: Eli Lilly and Company, Indianapolis, Ind.

[21] Appl. No.: 289,658

[22] Filed: Aug. 3, 1981

[51] Int. Cl.³ .................. A61K 31/78; A61K 47/00
[52] U.S. Cl. .................................... 424/81; 424/60; 424/167; 424/357; 424/358; 424/362; 424/365
[58] Field of Search ............................. 424/81, 358

[56] References Cited

U.S. PATENT DOCUMENTS

| | | | |
|---|---|---|---|
| 4,268,502 | 5/1981 | Martin | 424/83 |
| 4,268,526 | 5/1981 | Vargas et al. | 424/358 |
| 4,272,519 | 6/1981 | Herrold et al. | 424/83 |
| 4,272,544 | 6/1981 | Cella et al. | 424/273 |
| 4,278,570 | 7/1981 | Flom | 252/546 |

OTHER PUBLICATIONS

Elizabeth Arden, Product Line-SKIN DYNAMICS®-Everyday Moisture.
Elizabeth Arden, Product Line-SUN CARE®-Self Tanning Cream.
Elizabeth Arden, Product Line-CABRIOLE®-Body Lotion.
Elizabeth Arden, Product Line-CHLOE®-Satine Body Lotion.

*Primary Examiner*—Dale R. Ore
*Attorney, Agent, or Firm*—Karen B. O'Connor; Arthur R. Whale

[57] ABSTRACT

A method of decreasing the sensitivity of the skin without causing irritation is described, using a four component cosmetic regime. The four components comprising the regime are: a cleanser, a toner, a moisturizer, and a cream.

1 Claim, No Drawings

SENSITIVE-SKIN CARE REGIME

This invention relates to a novel sensitive-skin care regime, which protects the skin without skin irritation.

SUMMARY OF THE INVENTION

It is, therefore, an object of the present invention to provide a method of decreasing the sensitivity of sensitive skin without causing irritation, using a regime, which consists of the application to the skin of four components. The four components are: a cleanser, a toner, a moisturizer, and a cream.

DESCRIPTION OF THE PREFERRED EMBODIMENTS

In accordance with this invention there is provided a method of decreasing the sensitivity of sensitive skin without causing skin irritation, which comprises applying to the skin in a prescribed regime: a cleanser, a toner, a moisturizer, and a cream.

Each of the four components is a separate invention; the cleanser is claimed in application Ser. No. 289,657, filed Aug. 3, 1981; the toner is claimed in application Ser. No. 289,656, filed Aug. 3, 1981; the moisturizer is claimed in application Ser. No. 289,655, filed Aug. 3, 1981; and the cream is claimed in application Ser. No. 289,653, filed Aug. 3, 1981. In addition, a cream pack formulation is claimed in application Ser. No. 289,654, filed Aug. 3, 1981.

The order and timing of the use of the four products can be varied to suit individual needs. Some protection will be obtained even if all the formulations are not used or if there is a delay between usage.

The cleanser formulation consists essentially of, in percent by weight:

| Ingredients | Percent |
| --- | --- |
| propylene glycol | 6.00 |
| magnesium aluminum silicate | 1.00 |
| sodium carboxymethyl cellulose | 0.10 |
| glyoxyldiureide | 0.50 |
| polyoxyethylene (10) soya or tall oil sterols | 2.50 |
| polyoxyethylene (3) myristyl ether myristate | 15.00 |
| squalane (2,6,10,15,19,23-hexamethyltetracosane) | 12.00 |
| polydimethylcyclosiloxane | 12.00 |
| stearyl alcohol (1-octadecanol) | 1.50 |
| cetyl alcohol (1-hexadecanol) | 3.00 |
| glyceryl monostearate and polyoxyethylene (100) monostearate | 2.00 |
| preservative | q.s. |
| deionized eater | q.s. to 100% |

The toner formulation consists essentially of, in percent by weight:

| Ingredients | Percent |
| --- | --- |
| polyacrylic acid polymer (Carbopol No. 941) | 0.10 |
| glycerin | 2.00 |
| glyoxyldiureide | 0.30 |
| acetylated polyethylene (10) lanolin alcohol | 1.00 |
| cetyl/stearyl 2-ethylhexanoate | 1.00 |
| 98% triethanolamine | 0.10 |
| preservative | q.s. |
| deionized water | q.s. to 100% |

The moisturizer formulation consists, essentially of, in percent by weight:

| Ingredients | Percent |
| --- | --- |
| polyacrylic acid polymer (Carbopol No. 941) | 0.20 |
| glyoxyldiureide | 0.50 |
| polyoxyethylene (20) sorbitan fatty acid ester | 2.00 |
| cetyl alcohol (1-hexadecanol) | 2.00 |
| glyceryl monostearate | 1.25 |
| sorbitan trioleate | 5.00 |
| polyphenylmethylsiloxane | 2.50 |
| 2-ethylhexyl p-dimethylaminobenzoate | 2.00 |
| lavandin | 0.0032 |
| rosemary | 0.0066 |
| thyme | 0.0102 |
| 98% triethanolamine | 0.20 |
| squalane (2,6,10,15,19,23-hexamethyl tetracosane) | 1.50 |
| avocado oil | 2.50 |
| light mineral oil | 7.00 |
| di(2-ethylhexyl)adipate | 0.625 |
| 2-ethylhexyl stearate | 1.025 |
| 2-ethylhexyl palmitate | 0.850 |
| preservative | q.s. |
| deionized water | q.s. to 100% |

The cream formulation consists essentially of, in percent by weight:

| Ingredient | Percent |
| --- | --- |
| white beeswax | 2.00 |
| distilled lanolin alcohols | 0.50 |
| white petrolatum | 2.00 |
| triglyceryl diisostearate | 5.50 |
| squalane (2,6,1,0,15,19,23-hexamethyltetracosane) | 5.00 |
| light mineral oil | 6.00 |
| isopropyl myristate | 5.00 |
| polyethylene homopolymer (1500 m. wt., density 0.91 g/cc) | 3.00 |
| polysimethylcyclosiloxane | 3.00 |
| quaternary bentonite (Bentone. No. 38) | 0.40 |
| 70% sorbitol solution | 5.00 |
| glyoxydiureide | 0.50 |
| preservative | q.s. |
| deionized water | q.s. to 100% |

One skilled in the cosmetic formulation art will appreciate that various preservatives can be added to the formulations in sufficient quantities. These preservatives include the esters of p-hydroxy benzoic acid, such as methyl p-hydroxybenzoate, and propyl p-hydroxybenzoate; cis-1-(3-chloroallyl)-3,5,7-triaza-1-azoniaadamantane chloride; ethylenediaminetetraacetic acid (EDTA) and salts of EDTA; imidazolidinyl urea; sodium N-lauryl-$\beta$-iminodipropionate; and the like or any combination thereof. The total amount of preservative used can vary, but usually it is from about 0.3 to about 1.0 percent by weight.

In addition, color and essence can be included in the formulations as desired. Color additives would include both natural and artificial dyes, such as carotenoid derivatives, D+C, F, D+C colors, iron oxides, and the like, while essences can include any non-irritating natural and artificial oils, perfumes, and the like.

The formulations are both non-irritating and non-stinging, according to standard cosmetic testing procedures. The first procedure utilized was the Lanman-Maibach Cumulative Irritation Test, which is a 21-day patch irritation procedure as described by Dr. B. M. Lanman at the Joint Conference on Cosmetic Sciences, Apr. 21–23, 1968 in Washington, D.C. as further modified in Phillips, L., Steinberg M., Maibach, H., and Akers, W., *Toxicology and Applied Pharmacology* 21, 369–382 (1972). The non-stinging and desensitizing properties of the formulations were established by the Lactic Acid Sting Test as described in P. J. Frosch and A. M. Kligman: "A Method for Appraising the Stinging Capacity of Topically Applied Substances" *Journal of the Society of Cosmetic Chemists* 28, 197–209, May 1977. In addition, an ether cup probe test and soap challenge showed that the method of treating sensitive skin with the formulations caused the skin to be less sensitive.

Sensitive skin is defined as skin which is fragile, delicate, and reacts to certain cosmetics and fragrances. Also, sensitive skin is defenseless against such things as weather changes and the sun.

In general, the individual ingredients used in the formulations should be of a quality or purity (such as U.S.P. or N.F.) suitable for cosmetic use.

The formulations are prepared by mixing the ingredients according to conventional methods and the preparation of these formulations is described in the following examples. The examples are illustrative of the formulations, but are not to be construed as limiting the invention.

EXAMPLE 1

Cleanser

| Phase | Formulation: Ingredient | Percent by weight |
|---|---|---|
| A | deionized water | 43.03 |
|  | Allantoin (Sutton and Schuylkill, glyoxyldiureide) | 0.50 |
|  | methylparaben (methyl p-hydroxybenzoate) | 0.20 |
|  | ethylenediaminetetraacetic acid | 0.02 |
|  | imidazolidinyl urea | 0.30 |
| B | propylene glycol | 6.00 |
|  | Veegum K (R. T. Vanderbilt, magnesium aluminum silicate) | 1.00 |
| B | sodium CMC-7MF (Hercules, sodium carboxymethyl cellulose) | 0.10 |
| C | stearyl alcohol (1-octadecanol) | 1.50 |
|  | cetyl alcohol (1-hexadecanol) | 3.00 |
|  | Arlacel 165 (I.C.I. United States, glyceryl monostearate and polyoxyethylene (100) monostearate | 2.00 |
|  | POE (10) soya sterol (polyoxyethylene (10) soya sterols) | 2.50 |
|  | Standamul 1414E (Henkel, polyoxyethylene (3) myristyl ether myristate) | 15.00 |
|  | Robane (Robeco, squalane) | 12.00 |
|  | Silicone Fluid 344 (Dow Corning, polydimethylcyclosiloxane) | 12.00 |
|  | propylparaben (propyl p-hydroxybenzoate) | 0.10 |
|  | butylparaben (butyl p-hydroxybenzoate) | 0.10 |
| D | deionized water | 0.50 |
|  | Dowicil 200 (Dow Chemical, cis-1-(3-chloroallyl)-3,5,7-triaza-1-azoniaadamantane chloride) | 0.15 |

Procedure

Phase A is prepared in a jacketed tank equipped with a propeller stirrer and side-sweep mixer, heated to about 75°–80° C., and mixed until all the powders are dissolved. The gums of Phase B are added to the propylene glycol and mixed until a uniform slurry is obtained.

Phase B is slowly added to Phase A while mixing rigorously, but without aerating. The temperature is maintained at about 75°–80° C. and Phase AB is mixed until all the gums are dispersed.

The ingredients of Phase C are heated to about 75°–85° C. and mixed until all the waxes are melted and all the powders dissolved.

Phase C is added to Phase AB while both are at about 75°–80° C. Phase ABC is mixed with side-sweep and propeller stirrer for about 15 minutes at about 75°–80° C., avoiding aeration. Mixing is continued and Phase ABC is cooled to about 50°–55° C. Then Phase D is added, and the product is cooled to about room temperature while mixing.

EXAMPLE 2

Toner

| Phase | Formulation: Ingredient | Percent by weight |
|---|---|---|
| A | deionized water | 10.00 |
|  | Carbopol No. 941 (B. F. Goodrich, polyacrylic acid polymer) | 0.10* |
| B | deionized water | 82.90 |
|  | glycerin | 2.00 |
|  | methylparaben (methyl p-hydroxybenzoate) | 0.20 |
|  | Allantoin (Sutton and Schuylkill, glyoxyldiureide) | 0.30 |
|  | imidazolidinyl urea | 0.30 |
| C | acetylated polyoxyethylene (10) lanolin alcohol | 1.00 |
|  | Pur-Cellin Oil (Dragoco, cetyl/stearyl 2-ethylhexanoate) | 1.00 |
|  | propylparaben (propyl p-hydroxybenzoate) | 0.10 |
| D | deionized water | 2.00 |
|  | 98% triethanolamine | 0.10 |

*Concentration may be increased up to 0.15% to achieve viscosity specification.

Procedure

Phase A is prepared one day before the batch manufacture. The Carbopol is added very slowly to the deionized water while mixing vigorously. The mixing is continued until all the Carbopol is wetted. Then Phase A is mixed again before being added to Phase B.

The ingredients of Phase B are blended and then heated to about 70°–75° C. Phase B is mixed with simple agitation (i.e. propeller mixer) until all the powders are dissolved. Phase A is added to Phase B and mixed until uniform. The temperature is maintained at about 70°–75° C.

The ingredients of Phase C are blended and then heated to about 70°–75° C. The mixing continues until all the propylparaben is dissolved. (Phase C has a turbid-hazy appearance and must be kept under agitation.)

Phase C is added to Phase AB and mixed for a few minutes with simple agitation. Phase ABC is then cooled to about 45°–50° C. while mixing. Phase D is prepared by mixing the triethanolamine into the deionized water, and then Phase D is added to Phase ABC. Phase ABCD is mixed and cooled to about 30°–35° C.

EXAMPLE 3

Moisturizer

| Phase | Formulation: Ingredient | Percent by weight |
|---|---|---|
| A | deionized water | 10.00 |
|   | Carbopol No. 941 (B. F. Goodrich, polyacrylic acid polymer) | 0.20 |
| B | deionized water | 58.38 |
|   | imidazolidinyl urea | 0.30 |
|   | methylparaben (methyl p-hydroxybenzoate) | 0.25 |
|   | ethylenediaminetetraacetic acid | 0.05 |
|   | Allantoin (Sutton and Schuylkill, glyoxyldiureide) | 0.50 |
| C | Polysorbate 20 (polyoxyethylene (20) sorbitan fatty acid ester) | 2.00 |
| D | cetyl alcohol (1-hexadecanol) | 2.00 |
|   | Cerasynt SD (Van Dyk and Co., neutral, non-emulsifying glyceryl monostearate) | 1.25 |
|   | sorbitan trioleate | 5.00 |
|   | Robane (Robeco, squalane) | 1.50 |
|   | avocado oil | 2.50 |
|   | light mineral oil | 7.00 |
|   | Wickenol 163 (Wickhen Products, di(2-ethylhexyl)adipate-25%; 2-ethylhexyl stearate-41%; 2-ethylhexyl palmitate-34%) | 2.50 |
|   | Silicone Fluid No. 556 (Dow Corning, polyphenylmethylsiloxane) | 2.50 |
|   | Escalol 507 (Van Dyk and Co., 2-ethylhexyl p-dimethylaminobenzoate) | 2.00 |
|   | propylparaben (propyl p-hydroxybenzoate) | 0.15 |
| E | deionized water | 1.00 |
|   | Dowicil 200 (Dow Chemical, cis-1-(3-chloroallyl)-3,5,7-triaza-1-azoniaadamantane chloride) | 0.20 |
| F | lavandin | 0.0032 |
|   | rosemary | 0.0066 |
|   | thyme | 0.0102 |
| G | deionized water | 0.50 |
|   | 98% triethanolamine | 0.20 |

Procedure

Phase A is prepared one day before batch manufacture. The Carbopol is dispersed in the deionized water with high shear using a propeller mixer. The phase is stirred until completely hydrated and allowed to stand overnight. Phase A is stirred before added to Phase BCD.

All of the ingredients of Phase B were dissolved in the deionized water in a jacketed tank equipped with a homomixer and a sidesweep. Phase B is heated to about 75°–80° C. and then Phase C is added. The temperature of Phase BC is maintained at about 75°–80° C. (Phase BC may be cloudy or hazy.)

In a jacketed tank equipped with a propeller mixer, the ingredients of Phase D are melted and mixed together. Then Phase D is heated to about 75°–80° C., making sure that all the waxes are melted and the propylparaben dissolved.

Phase D is added to Phase BC and then homomixed and sideswept for 20 minutes. The temperature of Phase BCD is maintained at about 75°–80° C. The mixture is then cooled to about 40°–45° C. The homomixing is discontinued and Phase A is added slowly while mixing with the sidesweep.

Phase E is prepared by dissolving the Dowicil in the deionized water, then Phase E is added to Phase ABCD when Phase ABCD is homogeneous. After Phase ABCDE is homogeneous, Phase F is added.

Phase G is prepared by dissolving the triethanolamine in the deionized water. Then Phase G is added to Phase ABCDEF after Phase ABCDEF is homogeneous. Mixing is continued and then Phase ABCDEFG is cooled to about 25°–30° C.

EXAMPLE 4

Cream

| Phase | Formulation: Ingredient | Percent by weight |
|---|---|---|
| A | light mineral oil | 6.00 |
|   | Polyethylene 617 (Allied Chemical, polyethylene homopolymer, 1500 m. wt., density 0.91 g/cc, softening pt. 102° C., viscosity at 140° C. 145 cps) | 3.00 |
| B | white beeswax | 2.00 |
|   | Super Hartolan (Croda, distilled lanolin alcohols) | 0.50 |
|   | white petrolatum | 2.00 |
|   | Robane (Robeco, squalane) | 5.00 |
|   | Silicone Fluid 344 (Dow Corning, polydimethylcyclosiloxane) | 3.00 |
|   | triglyceryl diisostearate | 5.50 |
|   | isopropyl myristate | 5.00 |
|   | propylparaben (propyl p-hydroxybenzoate) | 0.10 |
| C | Bentone No. 38 (NL Industries, quaternary bentonite) | 0.40 |
| D | deionized water | 60.38 |
|   | 70% sorbitol solution | 5.00 |
|   | imidazolidinyl urea | 0.30 |
|   | Allantoin (Sutton and Schuylkill, glyoxyldiureide) | 0.50 |
|   | methylparaben (methyl p-hydroxybenzoate) | 0.20 |
| E | deionized water | 1.00 |
|   | Dowicil 200 (Dow Chemical, cis-1-(3-chloroallyl)-3,5,7-triaza-1-azoniaadamantane chloride) | 0.10 |
| F | Annatto, O.S. (natural orange dye, which is a carotenoid derivative dispersed in corn oil mono-glycerides of the fatty acids derived from vegetable oil; CI 75120) | 0.02 |

Procedure

All the ingredients of Phase A are combined and heated to about 90°–95° C. in a jacketed tank equipped with a propeller stirrer. Phase A is stirred rigorously until all of the Polyethylene 617 is dissolved and should be crystal clear with no undissolved particles. In a separate jacketed tank equipped with a propeller mixer, the ingredients of Phase B are melted together and heated to about 90°–95° C., making sure that all of the propylparaben is dissolved.

Next, Phase C is carefully sprinkled in Phase B and Phase BC is stirred vigorously to disperse the Bentone No. 38. Phase A is added to Phase BC, mixed, and maintained at about 90°–95° C.

In a jacketed tank equipped with a homomixer and sweep stirrer, the Phase D ingredients are dissolved in the deionized water of Phase D and then heated to 90°–95° C., making sure that all of the methylparaben is dissolved. Phase ABC is added to Phase D and mixed with the homomixer and sweep stirrer for about 15 minutes at about 90°–95° C. The product will become very viscous.

Mixing with the sidesweep and homomixer is continued and the product is cooled to about 40°–45° C. The Dowicil 200 is dissolved in the deionized water of Phase E and then Phase E is added to Phase ABCD.

Phase F is added and mixing is continued with the sidesweep only. The product is then cooled to about 30°–35° C.

We claim:

1. A method of decreasing the sensitivity of sensitive skin without causing skin irritation which comprises applying to the skin in a regime:

(a) a cleanser formulation consisting essentially of, in percent by weight:

| Ingredients | Percent |
| --- | --- |
| propylene glycol | 6.00 |
| magnesium aluminum silicate | 1.00 |
| sodium carboxymethyl cellulose | 0.10 |
| glyoxyldiureide | 0.50 |
| polyoxyethylene (10) soya or tall oil sterols | 2.50 |
| polyoxyethylene (3) myristyl ether myristate | 15.00 |
| squalane (2,6,10,15,19,23-hexamethyl-tetracosane) | 12.00 |
| polydimethylcyclosiloxane | 12.00 |
| stearyl alcohol (1-octadecanol) | 1.50 |
| cetyl alcohol (1-hexadecanol) | 3.00 |
| glyceryl monostearate and polyoxyethylene (100) monostearate | 2.00 |
| preservative | q.s. |
| deionized eater | q.s. to 100% |

(b) a toner formulation consisting essentially of, in percent by weight:

| Ingredients | Percent |
| --- | --- |
| polyacrylic acid polymer (Carbopol No. 941) | 0.10 |
| glycerin | 2.00 |
| glyoxyldiureide 0.30 acetylated polyethylene (10) | |
| lanolin alcohol | 1.00 |
| cetyl/stearyl 2-ethylhexanoate | 1.00 |
| 98% triethanolamine | 0.10 |
| preservative | q.s. |
| deionized water | q.s. to 100% |

(c) a moisturizer formulation consisting essentially of, in percent by weight:

| Ingredients | Percent |
| --- | --- |
| polyacrylic acid polymer (Carbopol No. 941) | 0.20 |
| glyoxyldiureide | 0.50 |
| polyoxyethylene (20) sorbitan fatty acid ester | 2.00 |
| cetyl alcohol (1-hexadecanol) | 2.00 |
| glyceryl monostearate | 1.25 |
| sorbitan trioleate | 5.00 |
| polyphenylmethylsiloxane | 2.50 |
| 2-ethylhexyl p-dimethylaminobenzoate | 2.00 |
| lavandin | 0.0032 |
| rosemary | 0.0066 |
| thyme | 0.0102 |
| 98% triethanolamine | 0.20 |
| squalane (2,6,10,15,19,23-hexamethyl tetracosane) | 1.50 |
| avocado oil | 2.50 |
| light mineral oil | 7.00 |
| di(2-ethylhexyl)adipate | 0.625 |
| 2-ethylhexyl stearate | 1.025 |
| 2-ethylhexyl palmitate | 0.850 |
| preservative | q.s. |
| deionized water | q.s. to 100% | and (d) a cream formulation consisting essentially of, in percent by weight:

| Ingredient | Percent |
| --- | --- |
| white beeswax | 2.00 |
| distilled lanolin alcohols | 0.50 |
| white petrolatum | 2.00 |
| triglyceryl diisostearate | 5.50 |
| squalane (2,6,1,0,15,19,23-hexamethyltetracosane) | 5.00 |
| light mineral oil | 6.00 |
| isopropyl myristate | 5.00 |
| polyethylene homopolymer (1500 m. wt., density 0.91 g/cc) | 3.00 |
| polysimethylcyclosiloxane | 3.00 |
| quaternary bentonite (Bentone. No. 38) | 0.40 |
| 70% sorbitol solution | 5.00 |
| glyoxydiureide | 0.50 |
| preservative | q.s. |
| deionized water | q.s. to 100% |

* * * * *

UNITED STATES PATENT AND TRADEMARK OFFICE
CERTIFICATE OF CORRECTION

PATENT NO. : 4,368,187

DATED : January 11, 1983

INVENTOR(S) : Merlyn G. Flom; Anne M. Herrold; Joe O. Martin; Anton A. Mentlik; Patricia P. Warrick It is certified that error appears in the above—identified patent and that said Letters Patent is hereby corrected as shown below:

Column 1, line 54, "eater" should read --water--.

Column 1, line 64, move "0.30" under column heading "Percent".

Column 2, line 40, "(2,6,1,0,15,19,23-" should read --(2,6,10,15,19,23---.

Column 2, line 45, "polysimethylcyclosiloxane" should read --polydimethylcyclosiloxane--.

Column 2, line 47, "glyoxydiureide" should read --glyoxyldiureide--.

Column 2, line 56, delete extra spaces.

Column 7, line 30, "eater" should read --water--.

Column 7, line 40, move "0.30" under column heading "Percent".

Column 8, line 30, "ingredient" should read --ingredients--.

Column 8, line 35, "(2,6,1,0,15,19,23-" should read --(2,6,10,15,19,23---.

UNITED STATES PATENT AND TRADEMARK OFFICE
CERTIFICATE OF CORRECTION

PATENT NO. : 4,368,187

DATED : January 11, 1983

INVENTOR(S) : Merlyn G. Flom; Anne M. Herrold; Joe O. Martin; Anton A. Mentlik; Patricia P. Warrick It is certified that error appears in the above-identified patent and that said Letters Patent are hereby corrected as shown below:

Column 8, line 40, "polysimethylcyclosiloxane" should read --polydimethylcyclosiloxane--.

Column 8, line 43, "glyoxydiureide" should read --glyoxyldiureide--.

Signed and Sealed this

Fourth Day of October 1983

[SEAL]

Attest:

GERALD J. MOSSINGHOFF

Attesting Officer     Commissioner of Patents and Trademarks